(12) United States Patent
Schärer et al.

(10) Patent No.: US 7,872,135 B2
(45) Date of Patent: Jan. 18, 2011

(54) METHOD FOR INTRODUCING A 1,2-DOUBLE BOND INTO 3-OXO-4-AZASTEROID COMPOUNDS

(75) Inventors: Norber Schärer, Oberentfelden AG (CH); Beat Webber, Zofingen (CH); Beat W Müller, Therwil/BL (CH)

(73) Assignee: Siegfried Ltd., Zofingen (CH)

( * ) Notice: Subject to any disclaimer, the term of this patent is extended or adjusted under 35 U.S.C. 154(b) by 1542 days.

(21) Appl. No.: 10/521,421

(22) PCT Filed: Jul. 2, 2003

(86) PCT No.: PCT/CH03/00435
§ 371 (c)(1),
(2), (4) Date: Aug. 29, 2005

(87) PCT Pub. No.: WO2004/007523
PCT Pub. Date: Jan. 22, 2004

(65) Prior Publication Data
US 2006/0100434 A1 May 11, 2006

(30) Foreign Application Priority Data

| Jul. 16, 2002 | (CH) | 1242/02 |
| Aug. 8, 2002 | (CH) | 1375/02 |
| Jan. 8, 2003 | (CH) | 0015/03 |

(51) Int. Cl.
*C07D 221/22* (2006.01)
(52) U.S. Cl. .................. 546/77
(58) Field of Classification Search .......... 546/77
See application file for complete search history.

(56) References Cited

U.S. PATENT DOCUMENTS

| 4,335,054 A * | 6/1982 | Blaser et al. ............. 558/377 |
| 4,760,071 A * | 7/1988 | Rasmusson et al. ........ 514/284 |
| 5,091,534 A * | 2/1992 | King et al. ............... 546/14 |
| 5,710,342 A | 1/1998 | Imre et al. |

FOREIGN PATENT DOCUMENTS

| EP | 0298652 A2 | 1/1989 |
| EP | 0428366 A2 | 5/1991 |

OTHER PUBLICATIONS

Wakselman, M. Di-t-butyl-dicarbonate, in Encyclopedia of Reagents for Organic Synthesis (posted online Apr. 15, 2001).*

(Continued)

*Primary Examiner*—Frederick Krass
*Assistant Examiner*—Adam Milligan
(74) *Attorney, Agent, or Firm*—Hoffmann & Baron, LLP

(57) ABSTRACT

A process for preparing 17β-substituted 4-azaandrost-1-en-3-one compounds of the general formula (I):

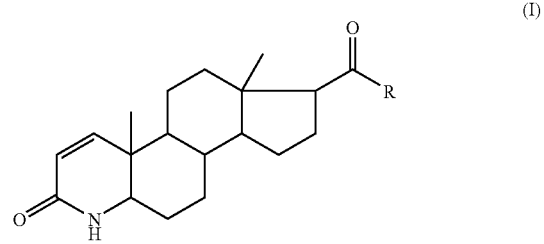

(I)

or a pharmaceutically approved salt thereof,
where
R is hydroxyl, optionally substituted, linear or branched ($C_1$-$C_2$)alkyl or ($C_1$-$C_{12}$)alkenyl; phenyl or benzyl; an —$OR_1$ radical, or an —$NHR_1$ radical, or an —$NR_1R_2$ radical;
$R_1$ is hydrogen, optionally substituted, linear or branched ($C_1$-$C_{12}$)alkyl or ($C_1$-$C_{12}$)alkenyl, or optionally substituted phenyl;
$R_2$ is hydrogen, methyl, ethyl or propyl; or
—$NR_1R_2$ is a 5- or 6-membered heterocyclic ring,
by (A) introducing protecting groups into the 3-keto-4-aza moiety of the corresponding 1,2-dihydro compound, so that a compound of the general formula (III) is formed:

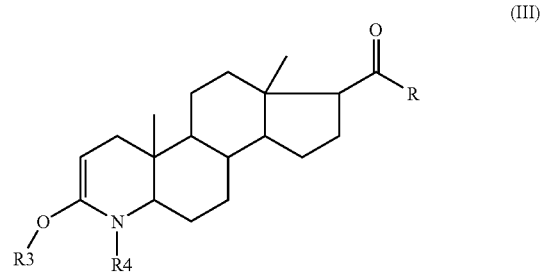

(III)

where
$R_3$ is trialkylsilyl or, together with $R_4$, the —C(O)—C(O)— or —C(O)—Y—C(O)— radical;
$R_4$ is alkyloxycarbonyl or phenyloxycarbonyl, preferably Boc (=tert-butyloxycarbonyl); or trialkylsilyl, or, together with $R_3$, the —C(O)—C(O)— or —C(O)—Y—C(O)— radical;
Y is —[C($R_5$)($R_6$)]$_n$— or —CH($R_5$)=CH($R_6$)—, or orthophenylene;
$R_5$ and $R_6$ are each independently hydrogen, linear or branched ($C_{1-8}$)alkyl or alkenyl, optionally substituted phenyl or benzyl; and
n is an integer of 1 to 4;
and where, in the case that R is hydroxyl, it has optionally reacted with a protecting group;
(B) reacting the resulting compound in the presence (i) of a dehydrogenation catalyst, and in the presence of (ii) optionally substituted benzoquinone, allyl methyl carbonate, allyl ethyl carbonate and/or allyl propyl carbonate, and
(C) removing the protecting groups $R_3$ and $R_4$ and optionally converting the resulting compound to a salt.

19 Claims, No Drawings

OTHER PUBLICATIONS

Fluck, New Notations in the Periodic Table, Pure & App. Chem. 60(3) 431-436, 1988.*

Ito et al. Synthesis of a,b-unsaturated carbonyl compounds by palladium(II)-catalyzed dehydrosilylation of silyl enol ethers. J. Org. Chem. 43(5), pp. 1011-1013, 1978.*

Minami et al. New synthetic methods for a,b-unsaturated ketones, aldehydes, esters, and lactones by the palladium-catalyzed reations of silyl enol ethers, ketene silyl acetals, and enol acetates with allyl carbonates. Tetrahedron 42(11) 2971-77, 1986.*

Rasmusson G.H., et al.: "Azasteriods; Structure-Activity Relationships for Inhibition of 5Alpha-Reductase and of Androgen Receptor Binding" Journal of Medicinal Chemistry, American Chemical Society, Washington, DC, U.S., vol. 29. No. 11, Nov. 1, 1986, pp. 2298-2315, XP000568779.

Bhattacharya, Apurba, et al.: "Silylation-Mediated Oxidation of 4-Aza-3-Ketosteroids With DDQ Proceeds Via DDQ-Substrate Adducts" Journal of the American Chemical Society, American Chemical Society, Washington, DC, U.S., vol. 110, 1988 pp. 3318-3319, XP002179347.

J. Tsuji, et al.: "Palladium Catalyzed Preparation or alpha.-Allyl Esters and alpha, beta-Unsaturated Esters From Saturated Esters Via Their Ketene Silyl Acetals" Tetrahedron Letters., vol. 25, No. 42, 1984, pp. 4783-4786, XP002226639.

* cited by examiner

METHOD FOR INTRODUCING A 1,2-DOUBLE BOND INTO 3-OXO-4-AZASTEROID COMPOUNDS

CROSS-REFERENCE TO RELATED APPLICATIONS

This application is the National Stage of International Application No. PCT/CH2003/000435, filed Jul. 7, 2003, which claims the benefit of Swiss Application Nos. CH 1242/02, filed Jul. 16, 2002, CH 1375/02, filed Aug. 8, 2002, and CH 0015/03, filed Jan. 8, 2003, the contents of which are incorporated by reference herein.

FIELD OF THE INVENTION

The present invention relates to a process for introducing a 1,2-double bond in 3-oxo-4-azasteroids by dehydrogenating 3-oxo-4-azasteroids saturated in the 1,2-position, in particular by dehydrogenating 17β-substituted 3-oxo-4-azasteroids to prepare the corresponding 17β-substituted 3-oxo-4-azasteroids which have a double bond in the 1,2-position.

BACKGROUND OF THE INVENTION

EP 0 155 096 discloses the preparation of 17β-substituted 4-aza-5-alpha-androstanes having a 1,2-double bond by oxidizing the corresponding 1,2-dihydro compound by means of benzeneselenic anhydride. Further processes for introducing a 1,2-double bond in 17β-substituted 4-aza-5-alpha-androstanes are, for example, also described in EP 0 298 652, EP 0 428 366 and EP 0 473 225. 17β-substituted 4-aza-5-alpha-androstanes having a 1,2-double bond are widely used pharmaceutically active compounds. Of significance is, for example, the compound 17β-(N-tert-butylcarbamoyl)-4-azaandrost-1-en-3-one (finasteride) which is used, for example, as a 5-alpha-reductase inhibitor for the treatment of benign prostate hyperplasia or of alopecia androgenitica. Also of significance is, for example, 17β-{N-[2,5-bis(trifluoromethyl)phenyl]}-4-azaandrost-1-en-3-one (dutasteride). The known processes for preparing these compounds have specific disadvantages, so that there is a need for improved alternative processes.

DETAILED DESCRIPTION OF THE INVENTION

The present invention relates to such an alternative preparation process.

The present invention is defined in the claims. The present invention relates to a process for preparing 17β-substituted 4-azaandrost-1-en-3-one compounds of the general formula (I):

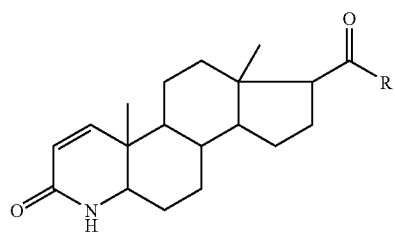

where
R is hydroxyl, optionally substituted, linear or branched ($C_1$-$C_{12}$)alkyl or ($C_1$-$C_{12}$)alkenyl; phenyl or benzyl; an —$OR_1$ radical, or an —$NHR_1$ radical, or an —$NR_1R_2$ radical;
$R_1$ is hydrogen, optionally substituted, linear or branched ($C_1$-$C_{12}$)alkyl or ($C_1$-$C_{12}$)alkenyl, or optionally substituted phenyl;
$R_2$ is hydrogen, methyl, ethyl or propyl; or
—$NR_1R_2$ is a 5- or 6-membered heterocyclic ring, and when R=hydroxyl also a pharmaceutically approved salt thereof, characterized in that
(A) protecting groups are introduced into the 3-keto-4-aza moiety (lactam moiety) of a compound of the general formula (II):

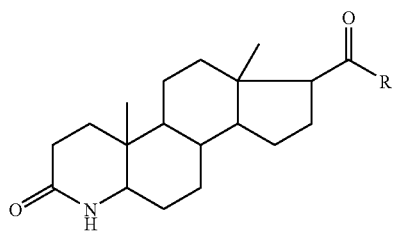

so that a compound of the general formula (III) is formed:

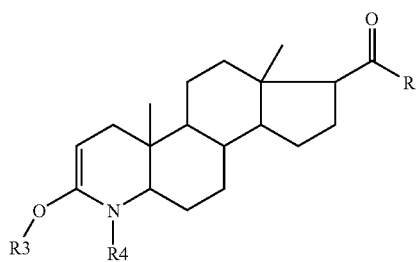

where
$R_3$ is trialkylsilyl or, together with $R_4$, the —C(O)—C(O)— or —C(O)—Y—C(O)— radical;
$R_4$ is alkyloxycarbonyl or phenyloxycarbonyl, preferably Boc (=tert-butyloxycarbonyl); or trialkylsilyl, or, together with $R_3$, the —C(O)—C(O)— or —C(O)—Y—C(O)— radical;
Y is —$[C(R_5)(R_6)]_n$— or —$CH(R_5)$=$CH(R_6)$—, or orthophenylene;
$R_5$ and $R_6$ are each independently hydrogen, linear or branched ($C_{1-8}$)alkyl or alkenyl, optionally substituted phenyl or benzyl; and
n is an integer of 1 to 4;

and where, in the case that R is hydroxyl, it has optionally reacted with a protecting group;
(B) the compound obtained [in step (A)] is reacted in the presence (i) of a dehydrogenation catalyst and in the presence of (ii) optionally substituted benzoquinone, allyl methyl carbonate, allyl ethyl carbonate and/or allyl propyl carbonate, and the $\Delta^1$ double bond is introduced in the 1-/2-position, and
(C) the protecting groups $R_3$ and $R_4$ are removed and when R=hydroxyl the resulting compound is optionally converted to a salt.

R is preferably linear or branched $(C_1-C_6)$alkyl, preferably methyl, ethyl, propyl or n-butyl, sec-butyl or tert-butyl, preferably tert-butyl; or an —$OR_1$ radical, or an —$NHR_1$ radical, or an —$NR_1R_2$ radical. Preference is given to the —$NHR_1$ radical.

When R is hydroxyl (or the —C(O)R radical is carboxyl), it is also possible in accordance with the invention to prepare a pharmaceutically approved salt of the compound of the formula (I), preferably an alkali metal salt, an alkaline earth metal salt or an ammonium salt, preferably a salt of sodium, potassium or ammonium, preferably a salt of sodium or potassium.

$R_1$ is preferably linear or branched $(C_1-C_6)$alkyl, or optionally substituted phenyl. $R_1$ as $(C_1-C_6)$alkyl is preferably methyl, ethyl, propyl, n-butyl, sec-butyl or tert-butyl, preferably tert-butyl. $R_1$ as optionally substituted phenyl is preferably mono(trifluoromethyl)phenyl or bis(trifluoromethyl)phenyl, preferably 2,5-bis(trifluoromethyl)phenyl.

In the —$NR_1R_2$ radical, $R_2$ is preferably methyl.

The —$NR_1R_2$ substituent as a 5- or 6-membered heterocyclic ring is preferably a radical of piperidine or pyrrolidine.

Preference is given to the —$NHR_1$ substituent where $R_1$ is tert-butyl or 2,5-bis(trifluoromethyl)phenyl.

$R_3$ is preferably trimethylsilyl or, together with $R_4$, the —C(O)—C(O)— or —C(O)—Y—C(O)— radical.

$R_4$ is preferably Boc, trimethylsilyl or, together with $R_3$, the —C(O)—C(O)— or —C(O)—Y—C(O)— radical. $R_4$ is preferably Boc or, together with $R_3$, the —C(O)—C(O)— or —C(O)—Y—C(O)— radical.

$R_4$ as alkyloxycarbonyl is preferably isobutyloxy-carbonyl, tert-butyloxycarbonyl, tert-amyloxycarbonyl, cyclobutyloxycarbonyl, 1-methylcyclobutyloxycarbonyl, cyclopentyloxycarbonyl, cyclohexyloxycarbonyl, 1-methylcyclohexyloxycarbonyl, preferably tert-butyloxycarbonyl.

$R_5$ and $R_6$ are preferably each independently hydrogen, linear or branched $(C_{1-4})$alkyl, or phenyl, preferably hydrogen, methyl, ethyl or propyl or phenyl.

n is preferably 1 or 2, preferably 1.

Y is preferably the —$CH(R_5)$— radical or ortho-phenylene, preferably methylene.

To introduce the trialkylsilyl protecting group, i.e. to silylate the NH group and/or the oxygen atom or the OH group [in step (A)], preference is given to using an $(alkyl)_3Si(halogen)$, e.g. $(CH_3)_3SiCl$, or bistrimethylsilyltrihaloacetamide, bistrimethylsilylacetamide, hexamethyldisilazane and/or bistrimethylurea, preferably bistrimethylsilyltrifluoroacetamide, or a trialkylsilyl trifluormethanesulfonate, preferably trimethylsilyl trifluoromethanesulfonate. The reaction conditions for the silylation are known from EP 0 473 226.

For the introduction of a protecting group where $R_3$, together with $R_4$, is the —C(O)—C(O)— or —C(O)—Y—C(O)— radical, the compound of the general formula (II) or the lactam moiety [in step (A)] is reacted with oxalyl chloride or malonyl chloride, of which oxalyl chloride is preferred. The reaction conditions for the reaction with oxalyl chloride are known from EP 0 428 366 and should be employed in an analogous manner for the reaction with malonyl chloride or analogously reacting compounds.

For the introduction of a protecting group where $R_4$ is alkyloxycarbonyl, e.g. tert-butyloxycarbonyl (Boc), the procedure is known per se, and is to react the compound of the general formula (II), for example, with Boc anhydride (Boc-O-Boc) $\{[(CH_3)_3C—O—C(O)]_2—O\}$ or with Boc carbamate $[(CH_3)_3C—O—C(O)—N(C_{1-4}—alkyl)_2]$. Here, Boc represents the other compounds reacting in the same way, i.e. compounds in which the tert-butyl radical has been replaced by another radical of the same reactivity, for example the tert-amyl, cyclobutyl, cyclopentyl or cyclohexyl radicals mentioned. Such analogous reactions are described numerously in the technical literature. When $R_3$ is trialkylsilyl and $R_4$ is Boc, the Boc protecting group is first introduced and silylation is effected afterward.

In step (B), the compound obtained in step (A) is reacted in the presence (i) of a dehydrogenation catalyst and in the presence of (ii) optionally substituted benzoquinone, allyl methyl carbonate, allyl ethyl carbonate and/or allyl propyl carbonate, and the $\Delta^1$ double bond is introduced in the 1-/2-position. The dehydrogenation catalyst is preferably selected from compounds (salts and complexes) of the group of the transition metals of the Periodic Table of the Elements, in particular selected from compounds of the metals of group VIII of the Periodic Table, in particular of iron (Fe), ruthenium (Ru) and osmium (Os); cobalt (Co), rhodium (Rh) and iridium (Ir); nickel (Ni), palladium (Pd) and platinum (Pt), and group IB, i.e. of copper (Cu), silver (Ag) and gold (Au). Preference is given to compounds of the metals of group VIII of the Periodic Table. Preference is given in particular to compounds or dehydrogenation catalysts based on rhodium (Rh), palladium (Pd) and platinum (Pt). Preference is given to palladium compounds. Examples of such palladium compounds are: Pd(0) compounds such as tris(dibenzylideneacetone)dipalladium-chloroform complex and Pd(II) compounds such as $PdCl_2$, $Pd(dppe)_2$, [dppe=bis(1,2-biphenylphosphino)ethane], $Pd(dppe)Cl_2$, $Pd(OAc)_2$, $Pd(dppe)(OAc)_2$, π-allyl-Pd complexes, preferably π-allyl-Pd chloride dimer. Preference is given to Pd(0) compounds, in particular tris(dibenzylideneacetone)dipalladium-chloroform complex. These compounds, or salts and complexes, are known per se and have been described in the literature.

For the thermal stabilization of the palladium complex, an additional complexing agent such as 2,2'-dipyridyl or 1,10'-phenanthroline may be used, preferably 2,2'-dipyridyl.

By way of explanation, it can be stated on the mechanism of catalysis that a Pd species adds at the carbon atom in the 2-position with elimination of the oxygen protecting group [for example of the —$Si(CH_3)_3$ group]. A subsequent beta-hydrogen elimination at the carbon atom in the 1-position leads to the desired $\Delta^1$ double bond in the 1-/2-position, and releases a further palladium species which is returned into the catalytic cycle. Indications for this reaction mechanism can be found in Tetrahedron Letters, page 4783 (1984). However, the present invention is not bound to this explanation.

The quinone used may also be a substituted quinone, for example a $C_{1-4}$-alkyl-, halogen-, cyano- or nitro-substituted quinone. Such quinones are known per se.

In step (C), the resulting compound is then converted to the compound of the formula (I) by removing the protecting groups introduced. This is effected preferably by treating with a suitable acid, for example with formic acid, acetic acid and/or trifluoroacetic acid, preferably with formic acid. Subsequently, the resulting compound may optionally be converted in a manner known per se to a pharmaceutically usable salt (where R=hydroxyl).

Preference is given to recrystallizing the resulting compound. This recrystallization may be carried out in apolar solvents such as benzine, heptane, hexane and toluene, preferably toluene. The compound of the formula (I) is in particular the compound mentioned at the outset, 17β-(N-tert-butyl-carbamoyl)-4-azaandrost-1-en-3-one (finasteride), which occurs in two polymorphic forms, specifically polymorphic form I and polymorphic form II, preference being given to form I. Form I is formed, for example, in the recrystallization of crude finasteride obtained in accordance with the invention from a saturated solution of toluene (about one part of crude finasteride in about six parts of toluene) on cooling to about 25° C. The polymorphic form II is formed, for example, in the recrystallization of crude finasteride obtained in accordance with the invention from a solution of toluene (about one part of crude finasteride in about six parts of toluene) on cooling to about 0° C.

The properties of 17β-{N-[2,5-bis(trifluoromethyl)phenyl]}-4-azaandrost-1-en-3-one (dutasteride) are known from the literature.

For the process described with the steps (A)-(C), the solvents used may be numerous organic anhydrous compounds, for example toluene, benzine, hexane, heptane, tert-butyl alcohol, diethyl ether, acetone, benzene, dioxane, tetrahydrofuran, chloroform, dimethylformamide or pyridine. The examples which follow illustrate the invention.

EXAMPLE 1

Substitution of dihydrofinasteride with Boc on the Nitrogen Atom of the 3-keto-4-aza moiety 10 g (26.7 mmol) of dihydrofinasteride are initially charged in tetrahydrofuran (THF) and cooled to −78° C. 15 ml (30 mmol) of lithium diisopropylamide solution (LDA solution) are metered into the resulting suspension and the clear solution is stirred for approx. 30 minutes. A solution of 6.7 g (30 mmol) of Boc anhydride in THF is then metered in. The solution is now allowed to warm to room temperature (RT). After the customary workup, a damp yellow powder is obtained which is stored in a drying cabinet overnight and used directly in example 2.

EXAMPLE 2

Silylation of the Compound Prepared in Example 1

1 g (2.1 mmol) of 4-Boc-dihydrofinasteride is dissolved in THF. 2.3 ml (4.6 mmol) of LDA solution are added under methanol-ice cooling to the clear yellow solution. The suspension is stirred for about 45 minutes, after which 0.46 g (4.2 mmol) of trimethyl-chlorosilane (TMSCl) is added dropwise at 18-20° C. The clear solution is concentrated and the residue taken up in heptane. After the filtration, the filtrate is concentrated as far as possible, and the resulting honey-brown oil is used in the following stage (example 3 and example 5).

EXAMPLE 3

Introduction of the $\Delta^1$ Double Bond to 4-benzyloxycarbonylfinasteride 0.145 g (0.65 mmol) of palladium acetate is dissolved and initially charged with 0.07 g (0.65 mmol) of benzoquinone in acetonitrile. 0.8 g (1.5 mmol) of the silyl compound prepared in example 3 is taken up in acetonitrile and added dropwise at an internal temperature (IT) of 20-25° C. The reaction mixture is stirred for 8 hours and purified using silica gel. The weakly colored clear solution is concentrated at ET 55-60° C. The resulting solid substance is used in example 4.

EXAMPLE 4

Removal of the Protecting Groups and Crystallization 0.5 g of the solid substance from example 3 is admixed with 20 g (0.175 mol) of trifluoroacetic acid and heated at reflux for about 15 hours. The trifluoroacetic acid is used as a reagent and as a solvent. After being cooled, the reaction mixture is poured onto a mixture of 300 g of saturated sodium bicarbonate solution and 50 g of ice and extracted with 20 g of ethyl acetate.

The brown crude product obtained in the preceding section a) is dissolved in toluene at 90° C. (toluene: crude material ratio=6:1), and cooled to 20-25° C. The precipitated, gray-white substance is filtered off at 20-25° C. and dried. Finasteride polymorph I is obtained.

EXAMPLE 5

Introduction of the $\Delta^1$ Double Bond to 4-benzyloxycarbonyl finasteride 2.0 g (3.7 mmol) of the compound from example 2 are admixed with 1.29 g (11.1 mmol) of allyl methyl carbonate in acetonitrile. The mixture is added dropwise to a solution, at 60-70° C., of 166 mg (0.74 mmol) of palladium(II) acetate in acetonitrile. After 1-2 hours at reflux, the mixture is worked up as described in example 3.3 g of solid substance are obtained.

EXAMPLE 6

Introduction of the $\Delta^1$ Double Bond 20 g (0.047 mol) of the oxalyl enol ether of dihydrofinasteride [compound IIIa where R=—NH-tert-butyl, $R_3$ and $R_4$=—C(O)—C(O)—] are heated to reflux temperature together with 16.3 g (0.140 mol) of allyl methyl carbonate and 76 g of anhydrous acetonitrile. 5 portions of a mixture of in each case 18 g of xylene and in each case 0.049 g of tris (dibenzylidineacetone)-dipalladium-chloroform complex (total molar amount of catalyst: 0.284 mmol) are added in succession. Each time, considerable gas evolution is visible when the addition is made. After refluxing for 12 h, the reaction is completed by adding two portions of a hot mixture of in each case 3 g of xylene and in each case 0.024 g of dehydrogenation catalyst (mixture heated slowly) (if necessary, further portions are added thereto). After the filtration, the reaction mixture is concentrated as far as possible, then 24.5 g of a yellow, honeylike material remain.

The honeylike material is taken up in 105 g of methanol and cooled to 0-5° C. 11.3 g (0.0403 mol) of 25% potassium methoxide solution are metered in slowly and the mixture is stirred at 0-5° C. internal temperature for approx. 1 hour. 20 g of water are then metered in and the cooling bath is removed; the internal temperature rises to 15-20° C. The mixture is concentrated to dryness, and 50 g of water, 90 g of toluene and 12 g of methanol are added to the solid residue which is heated to reflux temperature for 1 hour. After the stirrer has been switched off, the organic phase and water phase separate without any problem; the organic phase is removed while hot. The cooling to 25° C. within 2-4 hours brings the finasteride to crystallization in the polymorphic form I. After the drying, 8.1 g of white powder are obtained.

EXAMPLE 7

The procedure is analogous to the processes described in examples 1 to 6 when the $\Delta^1$ double bond is introduced into dihydrodutasteride, i.e. into a corresponding dihydro compound of the formula (I) where R is an —NHR, radical, and $R_1$ is 2,5-bis(trifluoro-methyl)phenyl, to obtain dutasteride by the introduction of the $\Delta^1$ double bond.

EXAMPLE 8

Preparation of methyl 3-oxo-4-aza-5α-androst-1-ene-17β-carboxylate

Stage 1 (Preparation of the Compound IIIb, i.e. A Compound of the Formula (III) where R=—OMe, $R_3$ and $R_4$=—C(O)—C(O)—)

2 g (0.005 mol, content >95%) of methyl 3-oxo-4-aza-5α-androst-1-ene-17β-carboxylate are admixed with 30 g of toluene and 2.6 g (0.019 mol) of oxalyl chloride are added slowly with cooling. Gradually, constant gas evolution sets in. The cloudy mixture is stirred overnight. From the clear reaction solution, excess oxalyl chloride and toluene are removed distillatively at room temperature under reduced pressure down to half of the original volume. As this is done, a white solid precipitates out which is filtered and washed intensively three times with 15 g each time of heptane. After the suction to dryness, 1.6 g of crude methyl ester remain. This is taken up in approx. 20 g of dichloromethane, the cloudy solution is washed intensively with 33 g of 5% potassium bicarbonate solution, the mixture is filtered and the organic phase is washed three times with 10 g each time of water. The clear, colorless organic phase is concentrated as far as possible and 0.9 g of the compound IIIb is obtained.

$^1$H NMR (200 MHz, CDCl$_3$, δ): 4.95 (1H, t); 3.68 (3H, s); 3.62-3.5 (1H, m); 3.22-3.06 (1H, m); 2.41-0.80 (17H, m); 0.97 (3H, s); 0.68 (3H, s)

Stage 2 (Introduction of the $\Delta^1$ Double Bond)

0.2 g (0.5 mmol) of the compound IIIb prepared in stage 1 is heated to reflux temperature (70-80° C.) together with 8 g of absolute acetonitrile, 1.5 g of chloroform, 0.18 g (1.5 mmol) of allyl methyl carbonate and 0.05 g (0.05 mmol) of palladium catalyst. Even in the course of heating, gas evolution is visible. After refluxing for approx. 30 minutes, the reaction mixture is concentrated as far as possible, the residue is taken up in a mixture of 15 g of methanol and 5 g of toluene and heated until there is a clear solution. After cooling to 0-5° C., a solution of 0.18 g (1 mmol) of 30% sodium methoxide solution in 2 g of methanol is metered in slowly and the clear solution is stirred for 1 hour. After the cooling bath has been removed, 3 g of water are added thereto and the cloudy mixture is stirred at room temperature for a further 1 hour. Afterward, the mixture is concentrated as far as possible and 10 g of toluene and 3 g of water are added to the residue. As soon as the mixture has separated into two clear phases in the course of heating, the organic phase was immediately removed and cooled. The addition of 2-4 g of heptane brings the product to crystallization. After the filtering, washing with approx. 5 g of heptane and suction to dryness, 34 mg of methyl 3-oxo-4-aza-5α-androst-1-ene-17β-carboxylate remain. $^1$H NMR (200 MHz, CDCl$_3$, δ): 6.81 (1H, d); 5.82 (1H, d); 5.48 (1H, s broad); 3.69 (3H, s); 3.4-3.35 (1H, m); 2.45-1.0 (17H, m); 0.97 (3H, s); 0.66 (3H, s)

EXAMPLE 9

Preparation of Dutasteride

Stage 1 (Preparation of 3-oxo-4-aza-5α-androstane-17β-carboxylic acid)

A suspension of 100 g (0.26 mol) of dihydrofinasteride, 480 g of 20% HCl solution (2.63 mol) and 120 g of methanol are heated to reflux and boiled intensively for 8-12 hours. The reactant goes into solution on heating; after 8 hours, there is a suspension which can be readily filtered. The filtercake is washed three times intensively with 100 g each time of water, suction-dried for approx. 15 minutes and subsequently dried overnight. Yield: 60 g.

$^1$H NMR (200 MHz, DMSO, δ): 11.95 (1H, s); 7.32 (1H, s); 2.95 (1H, m); 2.2 (2H, m); 2.0-0.85 (17H, m); 0.81 (3H, s); 0.62 (3H, s)

Stage 2 (Preparation of the Compound IIIc, i.e. A Compound of the Formula (III) where R=Cl, $R_3$ and $R_4$=—C(O)—C(O)—)

159 g (1.2 mol) of oxalyl chloride are added dropwise with cooling to a suspension of 40 g (0.12 mol) of the compound from stage 1 in 633 g of benzene within 20-30 minutes, and the suspension is stirred for 12 h (no further gas evolution visible). Benzene and excess oxalyl chloride are removed distillatively under reduced pressure at room temperature until the volume of the original solution has reduced to half. As this is done, a gray-white solid precipitates out which, after the filtration, is washed three times with 150 g each time of heptane and suction-dried for about 15 minutes. Yield: 37.1 g of the compound IIIc.

$^1$H NMR (200 MHz, CDCl$_3$, δ): 4.93 (1H, t); 3.58 (1H, m); 3.12 (1H, m); 2.88 (1H, m); 2.31-0.72 (18H, m); 0.97 (3H, s); 0.80 (3H, s)

Stage 3 (Preparation of the Compound IIId (R=—NH—(2,5—(CF$_3$)$_2$—C$_6$H$_3$), $R_3$ and $R_4$=—C(O)—C(O)—)

A suspension of 1.48 g (6 mmol) of bis-2,5-trifluoromethylaniline, 2.35 g (5.3 mmol) of the compound IIIc from stage 2 and 50 g of toluene is heated to reflux temperature (100-110° C.) for approx. 8 hours and then cooled. Toluene and aniline are removed distillatively at room temperature under reduced pressure until the volume of the original solution has reduced to half. 30 g of heptane are added to the suspension which is heated to 60-70° C. After one hour of intensive stirring, the mixture is suction filtered, and the filtercake is washed intensively four times with 10 g each time of heptane and suction dried for approx. 30-45 minutes. Yield: 1.7 g of the compound IIId.

$^1$H NMR (200 MHz, CDCl$_3$, δ): 8.79 (1H, s broad); 7.72 (1H, d); 7.49 (2H, m); 4.93 (1H, t); 3.59 (1H, m); 3.17 (1H, m); 2.38-1.0 (17H, m); 0.97 (3H, s); 0.81 (3H, s)

Stage 4 (Preparation of Dutasteride)

1 g (1.6 mmol) of the compound IIId from stage 3 is heated to reflux temperature (70-80° C.) together with 8 g of absolute acetonitrile, 2 g of chloroform, 0.55 g (4.8 mmol) of allyl methyl carbonate and 0.17 g (0.16 mmol) of palladium catalyst. Even in the course of heating, gas evolution is visible. After refluxing for approx. 30 minutes (no further gas evolution visible), the reaction mixture is concentrated as far as possible and the residue taken up in 5 g of methanol. After cooling to 0-5° C., a solution of 0.6 g (3.2 mmol) of 30% sodium methoxide solution in 4 g of methanol is metered in slowly and the clear solution is stirred at internal temperature 0-5° C. likewise for 1 hour. After the cooling bath has been removed, 3 g of water are added thereto, the mixture is stirred at room temperature for a further 1 hour, the cloudy mixture is concentrated as far as possible and 20 g of toluene and 6 g of water are added to the residue. The mixture is heated to reflux temperature. After 30 minutes, the clear organic phase is removed while hot and cooled to room temperature. The addition of 5-10 g of heptane brings the dutasteride to crystallization. After filtering, washing three times with 4 g each time of heptane and suction-drying, 0.3 g of dutasteride remains.

$^1$H NMR (200 MHz, CDCl$_3$, δ): 8.80 (1H, s broad); 7.75 (1H, d); 7.49 (2H, m); 680 (1H, d); 5.82 (1H, d); 8.80 (1H, s broad); 5.46 (1H, s broad); 3.35 (1H, m); 2.38-1.0 (17H, m); 0.97 (3H, s); 0.81 (3H, s)

What is claimed is:

1. A process for preparing 17β-substituted 4-azaandrost-1-en-3-one compounds of the general formula (I):

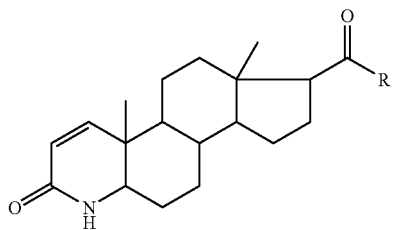

(I)

where
R is hydroxyl, optionally substituted, linear or branched (C$_1$-C$_{12}$)alkyl or (C$_1$-C$_{12}$)alkenyl; phenyl or benzyl; an —OR$_1$ radical, or an —NHR$_1$ radical, or an —NR$_1$R$_2$ radical;
R$_1$ is hydrogen, optionally substituted, linear or branched (C$_1$-C$_{12}$)alkyl or (C$_1$-C$_{12}$)alkenyl, or optionally substituted phenyl;
R$_2$ is hydrogen, methyl, ethyl or propyl; or
—NR$_1$R$_2$ is a 5- or 6-membered heterocyclic ring, and when R=hydroxyl also a pharmaceutically approved salt thereof,
characterized in that
(A) protecting groups are introduced into the 3-keto-4-aza moiety (lactam moiety) of a compound of the general formula (II):

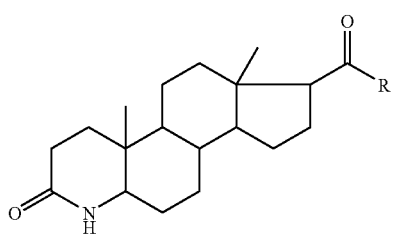

(II)

so that a compound of the general formula (III) is formed:

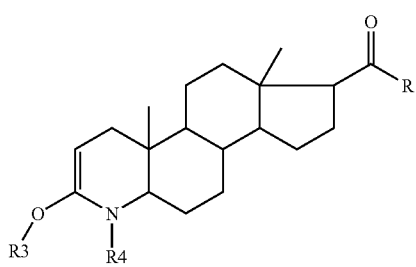

(III)

where
R$_3$ is trialkylsilyl or, together with R$_4$, the —C(O)—C(O)— or —C(O)—Y—C(O)— radical;
R$_4$ is alkyloxycarbonyl or phenyloxycarbonyl, Boc (=tert-butyloxycarbonyl); or tri-alkylsilyl, or, together with R$_3$, the —C(O)—C(O)— or —C(O)—Y—C(O)— radical;
Y is —[C(R$_5$)(R$_6$)]$_n$— or —CH(R$_5$)=CH(R$_6$)—, or ortho-phenylene;
R$_5$ and R$_6$ are each independently hydrogen, linear or branched (C$_{1-8}$)alkyl or alkenyl, optionally substituted phenyl or benzyl; and
n is an integer of 1 to 4;
and where, in the case that R is hydroxyl, it has optionally reacted with a protecting group;
(B) the compound obtained [in step (A)] is reacted in the presence (i) of a dehydrogenation catalyst selected from the group comprising catalytically active Pd(0) compounds, the tris(dibenzylidineacetone)dipalladium-chloroform complex and Pd(II) compounds. said Pd(II) compounds being selected from the group consisting of PdCl$_2$, Pd(dppe)$_2$, [dppe =bis(1.2-biphenyl phosphino)ethane], Pd(dppe)Cl$_2$, Pd(OAc)$_2$, and Pd(dppe)(OAc)$_2$ and from π-allyl-Pd complexes, including π-allyl-Pd chloride dimer, and mixtures thereof and in the presence of (ii) optionally substituted benzoquinone, allyl methyl carbonate, allyl ethyl carbonate and/or allyl propyl carbonate, and the Δ$^1$ double bond is introduced in the 1-/2-position, and
(C) the protecting groups R$_3$ and R$_4$ are removed and when R=hydroxyl the resulting compound is optionally converted to a salt.

2. The process of claim 1, characterized in that R is linear or branched (C$_1$-C$_6$)alkyl, methyl, ethyl, propyl or n-butyl, sec-butyl or tert-butyl; or an —OR$_1$ radical, or an —NHR$_1$ radical, or an —NR$_1$R$_2$ radical, —NH-tert-butyl, or optionally substituted phenyl.

3. The process of claim 1, characterized in that R$_1$ is linear or branched (C$_1$-C$_6$)alkyl, methyl, ethyl, propyl, n-butyl, sec-butyl or tert-butyl.

4. The process of claim 1, characterized in that R is an —NHR$_1$ radical where R$_1$ is 2,5-bis(trifluoromethyl)phenyl.

5. The process of claim 1, characterized in that the R$_2$ substituent in the —NR$_1$R$_2$ radical is methyl.

6. The process of claim 1, characterized in that the —NR$_1$R$_2$ substituent as a 5- or 6-membered heterocyclic ring is a radical of piperidine or pyrrolidine.

7. The process of claim 1, characterized in that R$_3$ is trimethylsilyl, or, together with R$_4$, is the —C(O)—C(O)— or —C(O)—Y—C(O)— radical.

8. The process of claim 1, characterized in that R$_4$ is selected from the group consisting of isobutyloxycarbonyl, tert-butyloxycarbonyl, tert-amyloxycarbonyl, cyclobutyloxycarbonyl, 1-methylcyclobutyloxycarbonyl, cyclopentyloxycarbonyl, cyclohexyloxycarbonyl, and 1-methylcyclohexyloxycarbonyl.

9. The process of claim 1, characterized in that R$_4$ is Boc, trimethylsilyl, or, together with R$_3$, the —C(O)—C(O)— or —C(O)—Y—C(O)— radical.

10. The process of claim 1, characterized in that R$_5$ and R$_6$ are each independently hydrogen, linear or branched (C$_{1-4}$) alkyl or phenyl methylene, and n is 1 or 2.

11. The process of claim 1, characterized in that in step (A) the compound of the general formula (II) is reacted with Boc anhydride or Boc carbamate.

12. The process of claim 1, characterized in that the dehydrogenation catalyst, is stabilized thermally by the presence of an additional complexing agent selected from 2,2'-bipyridyl or 1,10-phenanthroline.

13. The process of claim 1, characterized in that the benzoquinone used [in step (B)] is a substituted benzoquinone.

14. The process of claim 1, characterized in that [in step (C)] the introduced protecting groups are removed by treating with a suitable acid.

15. The process of claim 1, characterized in that [in step (C)] the resulting compound where R is hydroxyl is converted to an alkali metal salt, an alkaline earth metal salt, an ammonium salt.

16. The process of claim 1, characterized in that the resulting compound of the formula (I) is crystallized from an apolar solvent, said solvent being selected from benzene, heptane, hexane, toluene, and mixtures thereof.

17. The process of claim 1, characterized in that the resulting compound of the formula (I) which is 17β-(N-tert-butyl-carbamoyl)-4-azaandrost-1-en-3-one is crystallized from a saturated solution of toluene at a temperature of about 25° C.

18. The process of claim 1, characterized in that the resulting compound of the formula (I) which is 17β-(N-tert-butyl-carbamoyl)-4-azaandrost-1-en-3-one is crystallized from a saturated solution of toluene at a temperature of about 0° C.

19. The process of claim 1, characterized in that [in step (C)] the resulting compound where R is hydroxyl is converted to an ammonium salt, a salt of sodium, potassium or ammonium.

* * * * *